United States Patent [19]

Sun et al.

[11] Patent Number: 5,079,239

[45] Date of Patent: Jan. 7, 1992

[54] STEROL DISULFATES AND METHODS OF USE

[75] Inventors: H. Howard Sun, Glenmoore, Pa.; Sue S. Cross; Frank Koehn, both of Ft. Pierce; Malika Gunasekera, Vero Beach, Fla.

[73] Assignee: Harbor Branch Oceanographic Institution, Inc., Fort Pierce, Fla.

[21] Appl. No.: 481,489

[22] Filed: Feb. 16, 1990

[51] Int. Cl.$^5$ ............... C07D 71/00; A61K 31/58; A61K 31/57

[52] U.S. Cl. ............................. 514/174; 514/182; 540/72

[58] Field of Search ............ 540/72; 514/174, 182

[56] References Cited

U.S. PATENT DOCUMENTS

| | | | |
|---|---|---|---|
| 3,464,980 | 9/1989 | Brownfeild | 540/62 |
| 3,945,997 | 3/1976 | Cimarusti | 540/62 |
| 4,548,814 | 10/1985 | Rinehart | 514/2 |
| 4,731,366 | 3/1988 | Munro | 546/18 |
| 4,737,510 | 3/1988 | Rinehart | 514/388 |
| 4,808,590 | 2/1989 | Higa | 514/272 |
| 4,847,246 | 7/1989 | Wilson et al. | 514/175 |
| 4,935,439 | 6/1990 | Kashman et al. | 514/475 |
| 4,959,363 | 9/1990 | Wentland | 514/312 |

OTHER PUBLICATIONS

D. H. Faulkner (1984) Natural Products Reports 1:551–598.

D. H. Faulkner (1986) Natural Products Reports 3:1–33.

D. H. Faulkner (1987) Natural Products Reports 4:539–576.

Grant and Hackh's Chemical Dictionary [McGraw-Hill, New York, 1989] p. 14.

Merck Manual (Merck and Co. Rahway, N.J. 1987) pp. 190–191.

Reist et al. Nucleotides Analogues as Antiviral Agents, John Martin, Ed., American Chemical Society, Washington, D.C., 1990, pp. 17 to 33.

Haley et al., J. Natl. Cancer Inst. 74(4) 821-828, 1985, Biol. Absts., vol. 80, 1985, Abstract 32860.

*Primary Examiner*—Mukund J. Shah
*Assistant Examiner*—E. C. Ward
*Attorney, Agent, or Firm*—Saliwanchik & Saliwanchik

[57] ABSTRACT

Novel sterol disulfates have been isolated from the marine sponge *Petrosia weinbergii*. These compounds, and derivatives thereof, are useful antiviral compounds. One of these compounds is active against the AIDS virus and exhibits immunosuppressive activity.

13 Claims, No Drawings

STEROL DISULFATES AND METHODS OF USE

BACKGROUND OF THE INVENTION

Marine life has been the source for the discovery of compounds having varied biological activities. Some of the U.S. patents which have issued for such inventions are as follows: U.S. Pat. No. 4,548,814 for didemnins, having antiviral activity, were isolated from a marine tunicate; U.S. Pat. No. 4,731,366 discloses compounds, having antitumor properties, that were isolated from marine sponges from the genus Latrunculia; U.S. Pat. No. 4,808,590 discloses compounds, having antiviral, antitumor, and antifungal properties, isolated from the marine sponge Theonella sp.; and U.S. Pat. No. 4,737,510 discloses compounds, having antiviral and antibacterial properties, isolated from the Caribbean sponge *Agelas coniferin*. Clearly, marine sponges have proved to be a source of several bioactive compounds, and a number of publications have issued disclosing organic compounds derived from marine sponges, including Scheuer, P. J. (ed.) *Marine Natural Products, Chemical and Biological Perspectives*, Academic Press, New York, 1978-1983, Vol. I-V; Faulkner, D. J., (1984) Natural Products Reports 1:551-598; Natural Products Reports (1986) 3:1-33; Natural Products Reports (1987) 4:539-576; J. Am. Chem. Soc. (1985) 107:4796-4798. Though marine life has been the source of useful chemicals, there remains a need to discover more compounds which can be used medically to treat a wide range of diseases afflicting animals and humans.

Specifically, there is a great need for substances which can inhibit or kill viruses and retroviruses. Viruses and retroviruses are responsible for many serious diseases which cannot be effectively prevented or treated at this time. Viruses have been implicated in disorders ranging from the flu to cancer. Recently, RNA viruses have been associated with Acquired Immune Deficiency Syndrome (AIDS) and AIDS Related Complex (ARC). Specifically, the viruses responsible for these conditions are referred to as human immunodeficiency viruses (HIV). Although enormous sums of money and hours of manpower have been invested in an attempt to understand this disease, therapies and prophylactic compositions have proven to be extremely elusive.

The subject invention concerns sterol disulfates isolated from the marine sponge known as *Petrosia weinbergii*.

BRIEF SUMMARY OF THE INVENTION

The subject invention concerns novel sterol disulfate compounds and methods for use of these compounds. Specifically exemplified herein are five novel sterol disulfates designated HB99, HB100, HB123, HB124, and HB125, each of which has been isolated from the marine sponge *Petrosia weinbergii*. These compounds exhibited the ability to inhibit feline leukemia virus. HB99 was also found to be active against the AIDS virus and to have immunosuppressive activity. HB123, HB124, and HB125 have shown activity against influenza PR8 and in the coronavirus A59 assay. HB100 has also been shown to have antitumor activity. The isolation of these novel agents was performed by a combination of centrifugal countercurrent chromatography and high performance liquid chromatography. The chemical structures deduced from the spectral data as well as certain derivatives are shown in the Detailed Description of the Invention section.

The compounds of the subject invention, including derivatives thereof, have antiviral properties. Thus, they can be used for the treatment of a number of viral diseases including herpes and the common cold. Also, HB99 can be used to inhibit the AIDS virus. Furthermore, HB100 can be used to inhibit the growth of tumor cells.

DETAILED DESCRIPTION OF THE INVENTION

The subject invention pertains to novel chemical compounds isolated from marine sponges. These compounds have been shown to possess antiviral activity. Thus, the subject invention pertains to the compounds themselves, as well as pharmaceutical compositions containing these compounds. Also disclosed and claimed are methods for administering the novel compositions. Various derivatives of these compounds can be produced by known procedures. The parent compounds can be isolated from marine sponges as described below.

Isolation: The sponge *Petrosia weinbergii* (943 g) was collected at a depth of 100 feet off the S. W. tip of Acklin Island, Bahamas. *P. weinbergii* is classified as follows:
Phylum: Porifera
Class: Demospongia
Order: Haploscherida
Family: Petrosidae
Genus/species: *Petrosia weinbergii*

The *P. weinbergii* sample from which the novel compounds of the subject invention were isolated has the following characteristics: HBOI BMR Sample No. 17-VI-85-1-14: lamellate sponge, approximately 60 cm in diameter, 1 cm thick; oscules only on one side; surface smooth, but partially covered with orange zoanthids; color of oscular surface is tan, other side is green; internal color is tan; consistency firm, brittle, not compressible; spicules oxeas, skeletal arrangement as described by Van Soest, R. W. M. (1980) Marine Sponges from Curacao and Other Caribbean Islands 62(104):1-174. A sample of this sponge is on deposit at the Indian River Coastal Zone Museum, Fort Pierce, Fl.

The frozen sample was extracted with methanol-chloroform (1:1). After removal of the organic solvents, the aqueous suspension was sequentially extracted with ethyl acetate, n-butanol-ethyl acetate (1:1), and n-butanol. 1.1 g of the combined extract was fractionated by countercurrent chromatography on an Ito multilayer coil planet centrifuge ($CHCl_3$—i—PrOH—MeOH—$H_2O$, 9:2:12:10, lower phase stationary). Three of the resulting 60 fractions were rechromatographed on a Beckman C-18 HPLC column (MeOH—$H_2O$—$CHCl_3$, 60:40:5) to yield the sterol sulfates A and B (HB99 and HB100). Both compounds were recrystallized as white solids from MeOH—$H_2O$—$CHCl_3$(60:40:5).

An additional sample of *Petrosia weinbergi* (HBOI sample #7-VII-87-2-21), collected by SCUBA at 120 feet off Long Island in the Bahamas, was extracted with methanol and then with methanol-chloroform (1:1). The organic solvents were removed by evaporation and the aqueous suspension was partitioned with ethyl acetate and water. The water soluble fraction was subsequently partitioned between n-butanol and water. The butanol-soluble fraction was then chromatographed by C-18 reverse phase vacuum flash chromatography using a stepwise methanol-water gradient. Subsequent high pressure liquid chromatography on Vydac semipreparative C-18 reverse phase silica column in methanol-water (1:1), with refractive index detection, furnished sterol sulfates C (HB123), D (HB124), and E (HB125).

Spectral Data of the Sterol Disulfate A (HB99): mp. 182° C.; $[\alpha]_D^{20}=19.9$ (C=1.75, MeOH); high resolution FABMS: MH+ 681.2733 (calcd, $C_{30}H_{51}O_{10}S_2Na_2$, $\Delta 1.4$ mmu); low resolution EIMS 422 (M+ —2NaH-SO$_4$—H$_2$O, 4 rel. %), 407 (3), 404 (2), 379 (5), 360 (3), 295 (6), 271 (20), 253 (16), 211 (6), 193 (6), 161 (13), 157 (15), 147 (17), 133 (16), 119 (20), 105 (28), 91 (30), 81 (23), and 64 (100); IR: 3425, 2930, 1620, 1440, 1375, 1240, 1215, 1060, 970, 940, 880, 790 cm$^{-1}$; $^1$H NMR (CD$_3$OD): δ−0.20 (1H, dd, J=5.5, 4.2 Hz), 0.48 (1H, dd, J=8.6, 4.2 Hz), 0.68 (2H, m), 0.80–0.95 (3H, m), 0.99 (3H, s), 1.00 (3H, d, J=7.0 Hz), 1.03 (3H, d, J=7.0 Hz), 1.09 (3H, s), 1.10 (3H, d, J=6.7 Hz), 1.13–1.15 (2H, m), 1.18 (3H, s), 1.2–2.2 (19H, m), 4.52 (1H, m), 4.71 (1H, br m), and 4.74 (1H, br m); $^{13}$C NMR (CD$_3$OD): δ14.1 (q), 14.2 (q), 15.4 (q), 19.1 (d), 20.6 (t), 20.8 (q), 20.9 (q), 21.6 (t), 26.3 (t), 28.5 (t), 28.7 (s), 29.0 (t), 30.4 (t), 32.9 (t), 33.0 (d), 35.3 (d), 36.3 (s), 38.0 (t), 39.1 (t), 40.1 (d), 41.8 (t), 42.5 (t), 44.2 (s), 55.6 (d), 56.5 (d), 60.9 (d), 74.4 (d), 75.9 (d), 76.3 (d) and 78.1 (s).

The deduced structure of this compound is shown below.

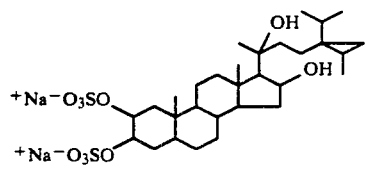

Spectral Data of the Sterol Disulfate B (HB100): mp. 191° C.; HRFABMS: M+ +Na 703.2570 (calculated for $C_{30}H_{50}O_{10}S_2Na_3$, $\Delta 4.0$ mmu); LREIMS: 441 (4), 422 (55), 410 (62), 404 (36), 392 (21), 379 (16), 310 (48), 297 (100), 285 (71), 269 (47), 257 (29), 187 (28), 173 (28), 157 (42), 145 (51), 133 (56), 119 (58), 105 (90), and 91 (82); $^1$H NMR (CD$_3$OD): δ−0.24 (1H, dd, J=5 Hz), 0.47 (1H, dd, J=8.5 Hz), 0.7–2.2 (m), 1.08 (3H, d, J=6 Hz), 3.55 (1H, d, J=11.5 Hz), 3.92 (1H, d, J=1.5 Hz), 4.22 (1H, m), 4.69 (1H, brm) and 4.72 (1H, brm); $^{13}$C NMR (CD$_3$OD): δ14.1 (q), 14.3 (q), 18.7 (q), 19.1 (d), 20.3 (t), 20.7 (q), 20.8 (q), 22.4 (t), 28.8 (s), 29.1 (t), 30.1 (t), 30.5 (t), 32.3 (d), 33.1 (d), 33.2 (t), 33.9 (t), 35.6 (d), 36.5 (s), 38.5 (t), 38.8 (t), 39.0 (t), 40.3 (d), 47.5 (d), 55.0 (d), 56.9 (d), 62.1 (d), 62.7 (t), 72.8 (d), 76.1 (d), and 76.4 (d).

The deduced structure of this compound is shown below.

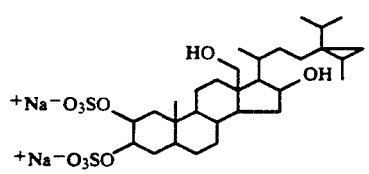

Spectral Data for Steroid C (HB123): HRFABMS: M+ +Na, m/z meas. 757.2630 (calcd. for $C_{33}H_{52}O_{11}S_2Na_3$, $\Delta 1.6$ mmu) $^1$H NMR 360 MHz, (CD$_3$OD): δ5.25 (1H, bq, J=6.8 Hz), 4.73 (1H,m), 4.69 (1H, m), 4.50 (1H, m), 4.20 (1H, dd, J=9.7, 3.4 Hz), 2.87 (1H, septet, J=7.1 Hz), 2.05 (5H, m), 1.80 (2H, m), 1.61 (3H, d, J=6.6 Hz), 1.70–1.35 (ca. 8H, bm), 1.32 (3H, s), 1.30–1.18 (4H, m), 1.13 (1H, dd, J=11.2, 6.6 Hz), 1.03 (3H, s), 1.00 (3H, d, J=6.6 Hz), 1.00 (3H, s), 0.98 (3H, d, J=6.7 Hz), 0.89 (3H, t, J=7.4 Hz), 0.74 (1H, m), 1.05–0.80 (4H, m), $^{13}$C NMR 90 MHz, (CD$_3$OD): δ141.9 (s), 120.3 (d), 84.5 (d), 83.5 (s), 76.4 (d), 76.1 (d), 73.1 (d), 58.5 (d), 56.6 (d), 55.8 (d), 43.4 (s), 41.2 (t), 40.2 (d), 39.4 (t), 39.1 (t), 36.4 (s), 35.5 (d), 34.2 (t), 33.4 (t), 33.0 (t), 30.5 (t), 29.8 (d), 29.0 (t), 21.5 (t), 21.2 (q), 21.1 (q), 19.0 (q), 17.9 (t), 15.0 (q), 14.4 (q), 14.3 (q), 13.1 (q).

The deduced structure of this compound is shown below.

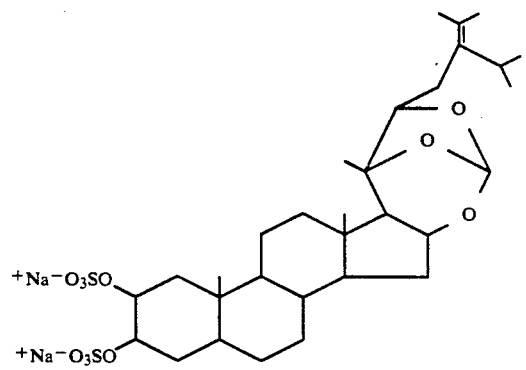

Spectral Data for Steroid D (HB124): HRFABMS: M+ +Na, m/z meas. 771.2867 (calcd. for $C_{34}H_{54}O_{11}S_2Na_3$, $\Delta 8.1$ mmu), $^1$H NMR 360 MHz, (CD$_3$OD): δ4.73 (1H, m), 4.63 (1H, m), 3.85 (1H, dd, J=10.5, 2.4 Hz), 2.05 (5H, m), 1.80 (2H, m), 1.65–1.20 (ca. 16H, bm), 1.29 (3H, s), 1.13 (3H, d, J=6.7 Hz), 1.12 (1H, m), 1.05 (1H, m), 1.03 (3H, s), 1.00 (3H, s), 1.00 (3H,d, J=6.7 Hz), 0.98 (3H, d, J=6.7 Hz), 0.97 (1H, m), 0.90 (1H, m), 0.89 (3H, t, J=6.7 Hz), 0.72 (1H, m), 0.66 (1H, dd, J=4.3, 8.6 Hz), −0.20 (1H, dd, J=5.5, 4.7 Hz), $^{13}$C NMR, 90 MHz, (CD$_3$OD): δ120.1 (s), 83.7 (d), 83.5 (s), 76.6 (d), 76.2 (d), 73.0 (d), 58.5 (d), 56.5 (d), 55.7 (d), 43.4 (s), 41.1 (t), 40.2 (d), 39.5 (t), 39.1 (t), 36.4 (s), 35.5 (d), 33.4 (d), 33.3 (t), 33.1 (t), 33.0 (t), 30.4 (t), 29.0 (t), 26.0 (s), 21.5 (t), 20.4 (d), 20.0 (t), 19.9 (q), 19.0 (q), 17.9 (d), 17.9 (t), 15.0 (q), 14.5 (q), 14.2 (q), 13.7 (q).

The deduced structure of this compound is shown below.

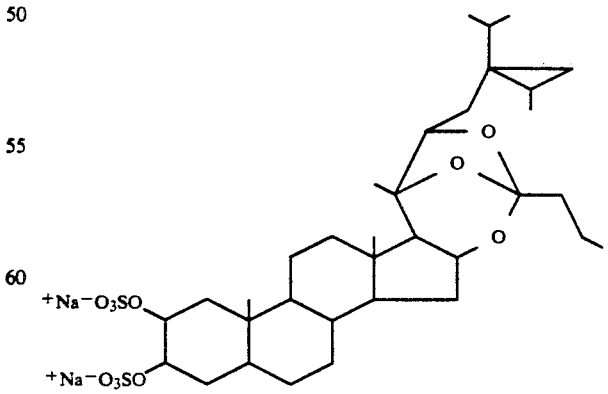

Spectral Data for Steroid E (HB125): LRFABMS: M+ +Na, m/z 759, $^1$H NMR 360 MHz, (CD$_3$OD): δ4.73 (1H, m), 4.68 (1H, m), 4.50 (1H, m), 4.05 (1H, dd, J=10, 3 Hz), 2.05 (5H, m), 1.88 (3H, s), 1.80 (2H, bt), 1.75-1.60 (ca. 6H, bm), 1.60-1.05 (ca. 8H, bm), 1.68 (3H, s), 1.02 (3H, s), 0.90 (3H, t, J=6.7 Hz), 0.89 (3H, t, J=6.7 Hz), 0.92 (3H, d, J=6.7 Hz), 0.80 (3H, d, J=6.7 Hz), 1.00-0.90 (ca. 4H, bm), 0.74 (1H, m), $^{13}$C NMR 90 MHz (CD$_3$OD): δ120.4 (s), 84.2 (d), 83.5 (s), 76.5 (d), 76.2 (d), 73.1 (d), 58.5 (d), 56.6 (d), 55.8 (d), 43.5 (s), 42.6 (d), 41.2 (t), 40.2 (d), 39.4 (t), 39.0 (t), 36.5 (s), 35.6 (d), 33.4 (t), 33.0 (t), 30.4 (t), 29.5 (d), 29.1 (t), 23.6 (t), 21.6 (t), 20.7 (q), 18.7 (q), 18.0 (t), 17.7 (q), 15.0 (a), 14.4 (q), 14.3 (q), 12.8 (q).

The deduced structure of this compound is shown below.

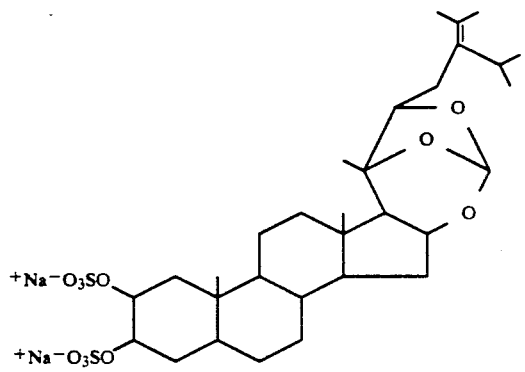

Derivatives of these isolated compounds can be prepared by procedures which are well known to those skilled in the art. Examples of these derivatives are represented by the following structures.

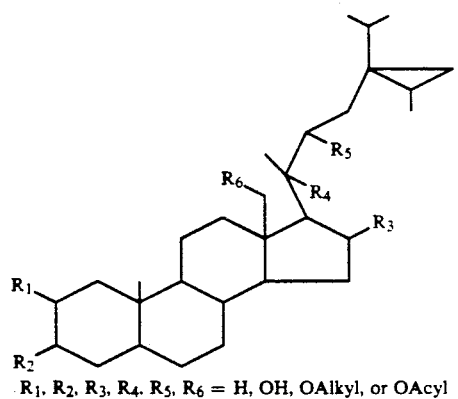

$R_1, R_2, R_3, R_4, R_5, R_6$ = H, OH, OAlkyl, or OAcyl

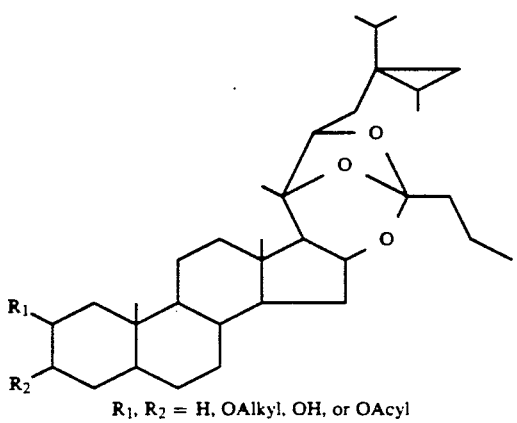

$R_1, R_2$ = H, OAlkyl, OH, or OAcyl

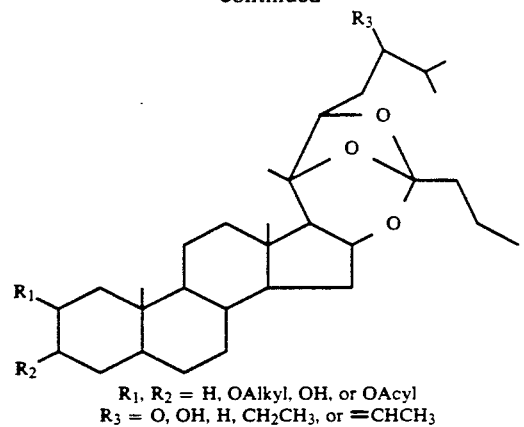

$R_1, R_2$ = H, OAlkyl, OH, or OAcyl
$R_3$ = O, OH, H, CH$_2$CH$_3$, or =CHCH$_3$

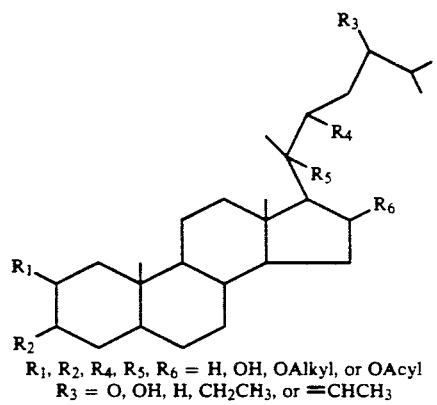

$R_1, R_2, R_4, R_5, R_6$ = H, OH, OAlkyl, or OAcyl
$R_3$ = O, OH, H, CH$_2$CH$_3$, or =CHCH$_3$ The novel compounds of the subject invention were each tested for activity against the feline leukemia virus (FeLV), against the human immunodeficiency virus (HIV), mouse coronavirus A59, and against influenza PR8. These assays and their results are described below. Unless otherwise indicated, the term "virus" as used here refers to both DNA and RNA viruses. HB100 was also tested for antitumor activity.

MATERIALS AND METHODS

Protocol for Feline Leukemia Virus (FeLV) Antiviral Drug Test.

Feline leukemia viruses belong to the retrovirus family. Diseases caused by members of this family in cats have clinical manifestations similar to symptoms observed in humans with diseases caused by the human immunodeficiency viruses. Feline leukemia virus was selected as a representative member of the retrovirus family to use as a model for drug testing to search for compounds effective in preventing viral infection and replication. Cell lines were provided by Hansen Veterinary Immunology, and reagents and protocols for the ELISA assay can be purchased from the same company.

Mechanics of Toxicity Assay

A. Determination of Toxicity of Samples for CRFK Cells with Neutral Red Assay or MTT Assay 1. Neutral red assay This assay is a modification of a procedure provided in detail by Dr. Ellen Borenfreund from Rockefeller University. Borenfreund, E., and J. A. Puerner (1984) "A Simple Quantitative Procedure Using Monolayer Cultures for Cytotoxicity Assays (HTD/NR-90)," J. Tissue Culture Methods 9:7-9.

a. Reagents

1) Neutral red (NR) prepared as a 0.4% aqueous stock solution. For assays a 1:100 dilution is prepared in Dulbecco's PBS.

2) Formol-calcium mixture: 1 ml 40% formaldehyde, 1 ml 10% anhydrous calcium chloride, and 98 ml water.

3) Acetic acid-ethanol mixture: 1.0 ml glacial acetic acid in 100 ml 50% ethanol.

b. Test

1) Remove fluid from plates, add 0.2 ml diluted neutral red, and incubate 3 hours at 37° C.

2) Remove neutral red and add 0.2 ml of the formol-calcium to remove unincorporated dye.

3) Add 0.2 ml of acetic acid-ethanol, shake, and read at 540 nm.

2. MTT Toxicity Assay

The use of the dye MTT has been found to be as satisfactory as neutral red and the actual values from the two assays are close.

a. MTT Sigma No. M-2128 listed as a mutagen [3-(4,5-dimethylthiazol-2-yl)-2,5-diphenyltetrazolium bromide]

b. MTT is diluted in D-MEM maintenance medium at a concentration of 1 mg per ml. For the toxicity test 75 microliters are added to each well of a 96-well plate without removing any medium. The plates are incubated for 6 hours at 37° C. At the end of the incubation period the medium is removed. If the cell layer is adherent, plates are not centrifuged to bring the cells down. CRFK is an adherent cell line, and for the MTT assay, no centrifugation is required. To each well 200 microliters of isopropyl alcohol are added. The formazan crystals are dissolved. After mixing, the plates are read with a plate reader at a wavelength of 570 nm. Toxicity percentages are determined the same as for neutral red.

Protocol for Antiviral Assay for Mouse Coronavirus A-59

The antiviral assay for A59 is a cytopathic test (CPE). Susceptible cells are infected with the virus at a dose that infects most of the cells and produces CPE. The characteristic CPE observed is the formation of syncytia. Compounds and extracts which inhibit the CPE are referred to as active samples.

A. Cell Culture

1. NCTC clone 1469 is a derivative of mouse liver.
2. ATCC No. CCL 9.1, freeze 2518, passage No. 16, frozen November 1980 at $2.4 \times 10^6$.

B. Virus

1. Mouse hepatitis virus strain MHV-A59 classified as a coronavirus.
2. ATCC No. 764.

C. Viral Assay

1. Dilute drug or extract for test in the appropriate solvent.
2. Add 20 μl per tube or well.
3. Allow the solvent to evaporate under the laminar flow hood.
4. Dilute the MHV-A59 in Dulbecco's phosphate buffered saline with $Ca^{++}$ and $Mg^{++}$ to the appropriate predetermined dilution for the lot number currently in use.
5. Remove medium from wells of 24 well plate containing NCTC 1469 cells seeded 24 hours earlier.
6. Medium can be removed by pouring the fluid from the plate and blotting it on a sterile towel.
7. Add 200 lambda of diluted virus to each test well. Add PBS to control wells.
8. Incubate cells and virus for 1 hour at 37° C.
9. Pour off supernatant at end of incubation period.
10. To each glass tube add 10 lambda of dimethyl sulfoxide (DMSO). The purpose for the DMSO is to solubilize the drug. If it is known that the drug under test is water soluble, then the DMSO is not necessary. However, in cases of testing unknown compounds, DMSO may be added, but DMSO causes some toxicity. Since differences have been noted with and without DMSO, the preferred technique is to test the sample under both conditions.
11. Add 1 ml of maintenance medium to each glass tube.
12. Pour the contents of the glass tube into the corresponding well of the tissue culture plate.
13. Incubate infected cells at 37° C. and read the following day.
14. At 12 hours, areas of cell fusion are quite apparent and can be detected both visually and microscopically.
15. At 24 hours the CPE is extensive, and on stained plates the difference between activity and none is apparent from visual examination.
16. To stain plates, discard medium and to each 16 mm well add 200 lambda of methylene blue stain or other appropriate stain.
17. Leave the stain on the cell sheet for 30 minutes or more.
18. Pour off the stain and wash plates in tap water until the water is clear.
19. Allow plates to dry. If it is desired, the plates can be kept as a permanent record for the experiment.
20. Scoring drug activity a. Cytotoxicity scoring 100% = complete cell destruction
75% = partial cell destruction
50% = partial cell destruction
25% = partial cell destruction
0% = no cytotoxicity b. % Antiviral activity To assist in visual interpretation of the data, the antiviral activity is scored from a minus to a three plus based on the percentage of inhibition of viral cytopathic effects. Antiviral activity on crude extracts and pure samples submitted for screens is expressed using these values and the toxicity values listed above.

+++ = complete inhibition of CPE and cell fusion
++ = partial inhibition
+ = partial inhibition
+/− = partial inhibition
− = no protection The $EC_{50}$, representing the concentration of drug that results in a 50% reduction of the viral cytopathic effect, and the $IC_{50}$, representing the concentration of the drug resulting in 50% growth inhibition, are determined from graphs constructed from the raw data. The in vitro therapeutic index (TI) is the ratio of $IC_{50}/EC_{50}$.

Protocol for Antiviral Assay for Influenza Virus Type A Strain PR8

The antiviral assay for influenze virus type A strain PR8 is a cytopathic effect (CPE) reduction assay based on dye uptake of normal viable cells compared to cells infected with PR8 virus. Canine kidney cells (MDCK) are infected with a viral dose that kills the cell population. Compounds with antiviral activity are identified by a decrease in CPE compared to the viral controls.

A. Cell Culture

The MDCK cell culture was obtained from the American Type Culture Collection as a frozen stock in DMSO and medium.

MDCK (Madin-Darby canine kidney cells): ATCC No. CCL 34, MDCK (NBL-2), Canine kidney (*Canis familiaris*), freeze #5305, passage 53. Assigned log number HB/SP 31.

B. Virus

Virus was obtained from the American Type Culture Collection. Myxovirus Influenza A strain A/PR/8/34 (HINI) ATCC VR 95. Freeze-dried virus lot 15D, passage history Fe/8, M/593, CE/172, equal quantities of allantoic fluid and 10% glucose and dextran. Original preparation contributed by A. Chappel/CDC. Isolate from patient in Puerto Rico, 1934. Francis, T. (1935) Proc. Soc. Exp. Biol. Med. 32:1172.

1. Passage of virus for stock pools: 150 cm sq. culture flasks are planted with 10 million cells and grown to confluency.

2. Cultures are washed with maintenance medium listed below. Virus is diluted 1:100 or 1:1000 in maintenance medium and 10 ml added to each flask. After 1 hour incubation period at 37° C., discard virus and add 50 ml maintenance medium. Incubate at 37° C. and harvest cells and fluid when cytopathic effects (CPE) affect the majority of the cells. Vial in 0.5 ml amounts and store at −70° C.

3. For viral assays, titrate the virus in 96-well plates. Wells are planted with 30,000 cells and allowed to reach near confluency by day 2. Dilute the virus in maintenance medium in 10-fold log steps. Add 100 microliters to each well at the appropriate dilution and incubate plates for three days. Cytopathic effects are scored as follows:

− = no CPE  
+ = <25% of cells show CPE  
++ = >25% and <50% of cells show CPE  
+++ = >50% and <75% of cells show CPE  
++++ = >75% and <100% of cells show CPE For the influenza antiviral assay, the most reproducible results are obtained by using a dosage of virus which produces 75–100% CPE.

C. Viral Assay

1. Preparation of expedition samples for screening a. Samples in ethanol, methanol, and other pretested solvents can be tested directly. Samples in solvents such as methanol/toluene mixtures must be evaporated and resuspended into an acceptable solvent.

2. Antiviral test. Tissue culture 96-well plates (Nunclon, USA) are planted at a cell concentration of 25,000 to 30,000 cells per well and grown for two days. Medium is withdrawn with an eight-place manifold (Wheaton Scientific, Milville, N.J.), and 100 µl of maintenance medium is added to rows B, D, F, and H. In alternate rows, 100 µl of the test samples are added to the antiviral test well and the drug control well. It is noted that after the incubation period the virus suspension is left on the cell layer. On day three the assay is read. For dilutions of the test drugs or samples, if a 10 mg per ml or 1 mg per ml suspension is submitted, the ratio of medium to drug for dilutions is 90 to 10 to obtain 100 µg or 1 µg of the test drug in the first well. From this well two-fold or ten-fold dilutions are prepared. Routine samples for screens are tested at 3 or 4 dilutions. Pure drugs are tested at sufficient concentrations to determine the 50% effective concentrations.

3. Results. Observe plates under the microscope for the overall condition of the MDCK cells and the progression of cytopathic effects in the viral controls. If the plates are in good condition, stain with neutral red and obtain optical density values at 540 nm wavelength.

a. Neutral red assay. This assay is a modification of a procedure provided in detail by Dr. Ellen Borenfreund from Rockefeller University (Borenfreund, E. and J. A. Puerner [1984] J. Tissue Culture Methods 9:7-9).

i. Materials  
Formaldehyde (40%) F-77-P  
Calcium chloride, anhydrous C-77  
Acetic acid, glacial A-38-S  
Alcohol, reagent A 962  
Neutral red (C.I. 50040, Basic Red 5, Sigma No. N-7005)  
Dynatech microplate reader with 540 nm filter  
Mini orbital shaker ii. Procedure  
Neutral red (NR) prepared as a 0.4% aqueous stock solution shielded from light by foil. For assays a 1:10 dilution is prepared in Dulbecco's PBS.

Formol-calcium mixture: 1 ml 40% formaldehyde, 1 ml 10% anhydrous calcium chloride, and 98 ml water. Mixture can be prepared with 10 ml 40% formaldehyde, 10 ml 10% anhydrous calcium chloride, and 80 ml water. If the virus in the assay is a potential human hazard and not inactivated by alcohol and chlorox, these concentrations should be used. Acetic acid-ethanol mixture: 1.0 ml glacial acetic acid in 100 ml 50% ethanol.

4. Test a. On day 3, remove fluid from plates with 8-place manifold and vacuum.

b. Add 0.2 ml PBS containing neutral red.

c. Incubate for 3 hours at 37° C.

d. Remove dye medium with 8-place manifold and vacuum.

e. Add 0.2 ml of the formol-calcium to remove unincorporated NR and enhance attachment of cells to substratum. Because fixation damages the lysosomes, limit the exposure to less than 3 minutes.

f. Add 0.2 ml of acetic acid-ethanol to each well and keep plate at room temperature to extract the dye. Plates are then shaken for a few seconds on the minishaker. Read plates on microplate reader with a 540 nm filter.

5. Mathematics a. Controls  
1 = Cells only and no NR  
2 = Cells only + drug  
3 = Cells only + NR  
4 = Cells + NR + Drug  
% Cytotoxicity = $[(3-1)-(4-2)/(3-2)] \times 100$ b. % Antiviral Activity  
5 = Cells + Virus + NR + Drug  
6 = Cells + Virus + NR  
% Antiviral Activity = $(5/3) \times 100$  
% Antiviral Activity = $(5/4) \times 100$ c. % Toxicity. To assist in visual reading of the data, the percentages are converted to one of five assigned values for toxicity. The converted values are given in the data files.

0–10=0  Non-toxic
10–35=25  Marginal toxicity
36–50=50  Partial toxicity
51–75=75  Partial toxicity
76–100=100  Total cell kill d. % Antiviral. To assist in visual interpretation of the data, the antiviral activity is scored from a minus to a three plus based on the percentage of inhibition of viral cytopathic effects. Antiviral activity on crude extracts and pure samples submitted for screens is expressed using these values and the toxicity values listed above. The $EC_{50}$, representing the concentration of drug that results in a 50% reduction of the viral cytopathic effect, and the $IC_{50}$, representing the concentration of drug resulting in 50% growth inhibition, are determined from graphs constructed from the raw data. The in vitro therapeutic index (TI) is the ratio of $IC_{50}/EC_{50}$.

| | | |
|---|---|---|
| 76–100 = +++ | Total inhibition of drug dose | |
| 51–75 = ++ | Partial inhibition | |
| 26–50 = + | Partial inhibition | |
| 11–25 = +/− | Partial inhibition | |
| 0–10 = − | Negative | |

PROTOCOLS FOR IMMUNOMODULATORY ASSAY

The pure compound was tested in the two-way mixed lymphocyte reaction (MLR) and a lymphocyte viability assay (LCV) at 500, 50, 5, and 0.5 μg/ml, using murine splenocytes. Cellular proliferation was measured using incorporation of $^3$H-thymidine. Responses were reported as a percent of the positive MLR or LCV control.

I. Mixed Lymphocyte Reaction

1. Murine splenocyte suspensions were prepared separately from BALB/c and C57BL/6J mice. Spleens were aseptically removed and homogenized in RPMI 1640 tissue culture medium (TCM), supplemented with 10% fetal calf serum, 2% 1-glutamine, 15 mM HEPES, 1% antibiotic-antimycotic solution, and 25 μg/ml gentamycin (GIBCO). The cell concentrations were adjusted to $2.5 \times 10^6$ cells/ml. Aliquots of each cell population were removed to separate tubes, and the remaining two cell suspensions combined to one tube.

2. Serial, $\log_{10}$ dilutions of the pure compound were made in absolute ethanol, and 10 μl of each dilution were added to wells of microtiter test plates, and allowed to dry.

3. A volume of 0.2 ml of the combined splenocyte suspensions was added to triplicate test wells. Positive control wells received combined splenocyte suspensions in the absence of the test compounds. Negative control wells consisted of separate (not mixed) splenocyte suspensions cultured in the absence of the test compounds.

4. Plates were incubated in 5% $CO_2$ at 37° C. for 86 hours.

5. A volume of 0.05 ml of $^3$H-thymidine (20 (μCi/ml) was added to each well, and the plates incubated in 5% $CO_2$ at 37° C. for an additional 5 hours.

6. The contents of each well of the microtiter plates were harvested onto glass fiber filter strips, and the resulting filter discs placed in scintillation vials to which 2.0 ml of scintillation fluid was added.

7. The amount of incorporated $^3$H-thymidine was determined by counting the vials in a liquid scintillation counter.

8. Triplicate counts were averaged, and the data reported as a percentage of the positive control. A value of less than 100% of the positive control MLR with a corresponding LCV value of >70% suggests immunosuppressive effects of the compound. A value of greater than 150% of the positive MLR control with a corresponding LCV value of >75% suggests immunostimulatory effects of the compound.

II. Lymphocyte Viability Assay

1. Compounds were similarly tested in parallel with the MLR to determine their toxic effects on lymphoid cells using the lymphocyte viability assay (LCV).

2. Serial, $\log_{10}$ dilutions of the pure compound were made in absolute ethanol, and 10 μl of each dilution was added to wells of microtiter test plates, and allowed to dry.

3. Murine splenocyte suspensions were prepared from BALB/c mice. Spleens were aseptically removed and homogenized in RPMI 1640 tissue culture medium (TCM), supplemented with 10% fetal calf serum, 2% 1-glutamine, 15 mM HEPES, 1% antibiotic-antimycotic solution, and 25 μg/ml gentamycin (GIBCO). The cell concentrations were adjusted to $2.5 \times 10^6$ cells/ml.

4. A volume of 0.2 ml of the splenocyte suspension was added to replicate test wells. Positive control wells received splenocyte suspensions in the absence of the test compounds.

5. Plates were incubated at 37° C. for 86 hours. At the end of the incubation period, a volume of 75 μl of a 2.0 mg/ml solution of M.T.T. was added to each well, and the plates returned to the incubator for an additional 5 hours.

6. The supernatants from each micro well were then removed, and a volume of 200 μl of isopropanol was added and the contents mixed.

7. Values were obtained by comparing the optical densities (determined at 570 and 650 nm) of wells containing the test compounds with those of wells containing cells and medium only (positive control). The results are expressed as a percentage of the positive control.

8. Replicate counts were averaged, and the data reported as a percentage of the positive control. An LCV value of less than 70% of the positive control suggests cytotoxicity of the test compounds for lymphoid cells.

Following are examples which illustrate procedures, including the best mode, for practicing the invention. These examples should not be construed as limiting. All percentages are by weight and all solvent mixture proportions are by volume unless otherwise noted.

EXAMPLE 1

Results of FeLV Antiviral Drug Test and AIDS Antiviral Assay

Antiviral activity on crude extracts is expressed by percent antiviral activity or by using the minus and plus values stated above. The $EC_{50}$ of an antiviral drug represents the concentration of drug that results in 50% reduction of the viral cytopathic effect and the $IC_{50}$ represents the concentration resulting in 50% growth inhibition. These values are determined from graphs constructed from the raw data. The in vitro therapeutic index (TI) is the ratio of $IC_{50}/EC_{50}$.

The samples assayed were fractions HSA-15-2 (HB99) and HSA-15-3 (HB100), pure compounds HSA-42-2 (HB99) and 8MG45-1 (HB100), as well as HB123, HB124, and HB125.

The results of the assays are shown in Tables 1 through 3.

TABLE 1

FeLV assay of crude extracts containing the compounds of interest

| | Antiviral Activity (%) |
|---|---|
| Fraction HSA-15-2 (contains HB99) | 70 |
| Fraction HSA-15-3 (contains HB100) | 68 |

TABLE 2

FeLV assay of pure compounds.

| | $EC_{50}$ (μg) | $IC_{50}$ (μg) | TI |
|---|---|---|---|
| HB99 | 4 | 70 (514 μM) | 17.5 |
| HB100 | 5.2 | 37 (272 μM) | 7.1 |
| HB123 | 1 | >10 (>68 μM) | >10 |
| HB124 | 1.25 | >10 (>68 μM) | >8 |
| HB125 | 1 | >10 (>68 μM) | >10 |

TABLE 3

HIV assay for HB99

| $EC_{50}$ (μg) | $IC_{50}$ (μg) | TI |
|---|---|---|
| HB99 | | |
| 1 | 70 | 70 |

As can be seen in Tables 1 through 3, HB99, HB100, HB123, HB124, and HB125 all showed activity against the feline leukemia virus. HB99 also showed activity against the AIDS virus.

EXAMPLE 2

Results of Antiviral Assay for Mouse Coronavirus A-59

As shown in Table 4, HB123, HB124, and HB125 were assayed for activity against coronavirus A59. At 20 μg, each of the three compounds was able to significantly inhibit viral growth.

TABLE 4

Coronavirus A59 assay of pure compounds.

| HB123 | 20 μg toxicity = 25%, | activity = ++ |
|---|---|---|
| | 2 μg toxicity = 0, | activity = − |
| HB124 | 20 μg toxicity = 25%, | activity = ++ |
| | 2 μg toxicity = 0, | activity = − |
| HB125 | 20 μg toxicity = 0, | activity = ++ |
| | 2 μg toxicity = 0, | activity = − |

EXAMPLE 3

Results of Antiviral Assay for Influenza Virus Type A Strain PR8

As shown in Table 5, each of the three compounds tested caused total inhibition of the viral cytopathic effects. Even at 20 μg, no toxic effects were observed.

TABLE 5

Influenza PR8 assay of pure compounds.

| HB123 | 20 μg toxicity = 0, | activity = +++ |
|---|---|---|
| | 2 μg toxicity = 0, | activity = − |
| HB124 | 20 μg toxicity = 0, | activity = +++ |
| | 2 μg toxicity = 0, | activity = − |

TABLE 5-continued

Influenza PR8 assay of pure compounds.

| HB125 | 20 μg toxicity = 0, | activity = +++ |
|---|---|---|
| | 1 μg toxicity = 0, | activity = − |

EXAMPLE 4

Results of Immunomodulatory Assay

As shown in Table 6, HB99 exhibited immunosuppressive activity (MLR <100% and LCV >70%) at concentrations of 50 μg/ml and 5 μg/ml.

TABLE 6

Immunomodulatory data for steroid A (HB99)

| Dose (μg/ml) | % MLR | % LCV |
|---|---|---|
| 500.00 | 0 | 16 |
| 50.00 | 19 | 81 |
| 5.00 | 98 | 92 |
| 0.05 | 126 | 104 |

EXAMPLE 5

Antitumor Activity

HB100 has also been tested to determine its activity in inhibiting the growth of tumor cells. HB100 was found to inhibit the growth of tumor cells. Specifically, in the standard P388 assay, HB100 was found to have an $IC_{50}$ of 0.1 μg/ml.

EXAMPLE 6

Uses and Formulations

The compounds of the invention are useful for various non-therapeutic and therapeutic purposes. It is apparent from the in vitro testing that the compounds of the invention are effective for inhibiting the growth of tumor cells and for inhibiting viral growth and for controlling virus-related diseases in humans and animals. The diseases include herpes, the common cold, and AIDS. Also, these compounds could be used to inhibit the growth of plant viruses. Because of the antiviral properties of the compounds, they are also useful to swab laboratory benches and equipment in a virology laboratory to eliminate the presence of viruses. As disclosed herein, they are also useful prophylactically and therapeutically for treating viral infections in animals and humans. Also, HB99 has been shown to exhibit immunosuppressive activity.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration ot a host in the above indications will be dependent upon the identity of the viral infection, the type of host involved, its age, health, weight, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

Examples of such carriers for use in the invention include ethanol, dimethyl sulfoxide, glycerol, silica, alumina, starch, and equivalent carrier and diluents. While effective amounts may vary, as conditions in which such compositions are used vary, a minimal dosage required for antiviral activity is generally between 50 and 200 micrograms against 25-80 plaque-forming units of virus. To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The compounds of the subject invention can be parenterally, orally, or topically administered to subjects requiring antiviral treatment. The active compounds may be mixed with physiologically acceptable fluids such as saline or balanced salt solutions. Also, solid formulations such as tablets or capsules can be made.

The compounds of the subject invention may be applied, for example, orally, intravenously, intramuscularly, intraperitoneally, intranasally, intradermally, or subcutaneously. The compounds of the subject invention may also be combined with other antiviral substances to provide enhanced treatment.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. The compound HB123, having the following structural formula:

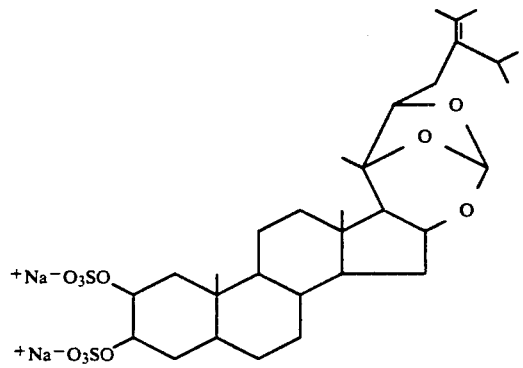

2. The compound HB124, having the following structural formula

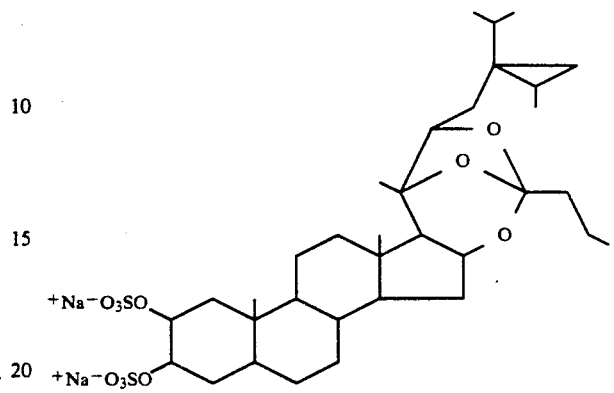

3. The compound HB125, having the following structural formula

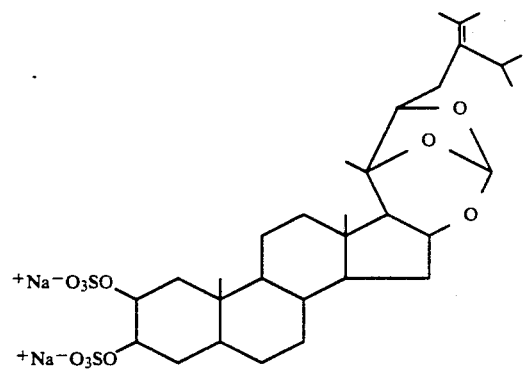

4. A compound having the following structural formula

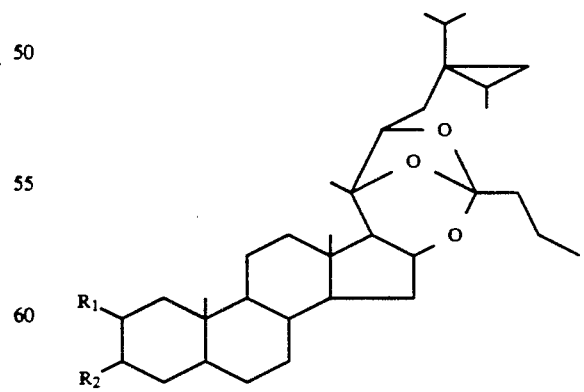

wherein $R_1$ and $R_2$ can be H, OH, or OAlkyl.

5. A compound having the following structural formula

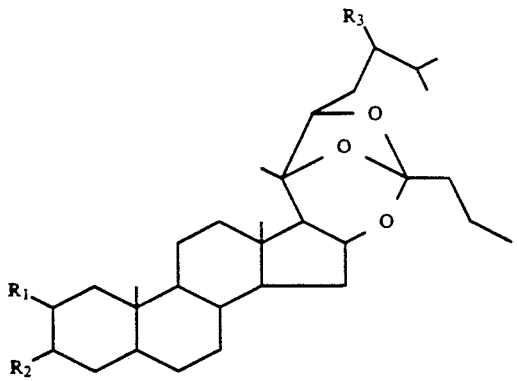

wherein $R_1$ and $R_2$ can be H, OH, or OAlkyl; and $R_3$ can be =O, OH, H, $CH_2CH_3$ or =$CHCH_3$.

6. A process for inhibiting or killing viruses selected from the group consisting of FeLV, HIV, myxovirus, and coronavirus, said process comprising the application of a compound selected from the group consisting of HB99, HB100, HB123, HB124, HB125 to said viruses.

7. The process, according to claim 6, wherein said compound is HB99 or derivatives thereof.

8. The process, according to claim 6, wherein said compound is HB100 or derivatives thereof.

9. The process, according to claim 6, wherein said compound is HB123, or derivatives thereof.

10. The process, according to claim 6, wherein said compound is HB124, or derivatives thereof.

11. The process, according to claim 6, wherein said compound is HB125, or derivatives thereof.

12. The process, according to claim 6, wherein said virus is the HIV virus.

13. The process, according to claim 12, wherein said compound is HB99.

* * * * *

UNITED STATES PATENT AND TRADEMARK OFFICE
CERTIFICATE OF CORRECTION

PATENT NO. : 5,079,239

DATED : January 7, 1992

INVENTOR(S) : H. Howard Sun, Sue S. Cross, Frank Koehn, Malika Gunasekera

It is certified that error appears in the above-identified patent and that said Letters Patent is hereby corrected as shown below:

Column 4: line 4: "(4H. m)" should read --(4H, m)--; line 5: "(s), 120.3 (d)" should read --(s), 120.3 (s), 120.2 (d)--; line 15:

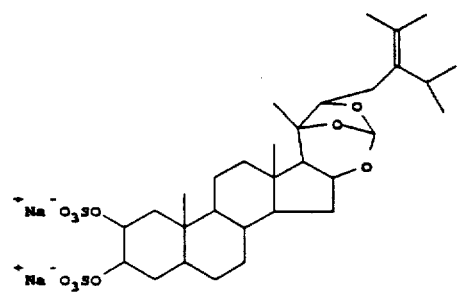 should read 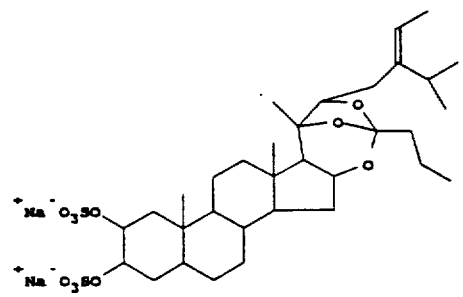

Column 5: line 3: "(3H, s), 0.90" should read --(3H, s), 1.02 (3H, s), 0.90--

UNITED STATES PATENT AND TRADEMARK OFFICE
CERTIFICATE OF CORRECTION

PATENT NO.   :   5,079,239

DATED        :   January 7, 1992

INVENTOR(S)  :   H. Howard Sun, Sue S. Cross, Frank Koehn, Malika Gunasekera

It is certified that error appears in the above-identified patent and that said Letters Patent is hereby corrected as shown below:

Column 5:   line 15:

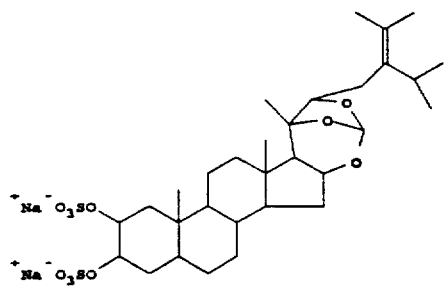   should read   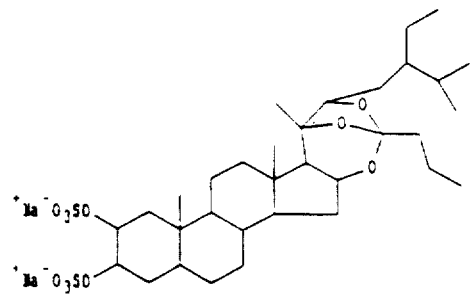

Column 8:   line 66: "influenze" should read --influenza--.

UNITED STATES PATENT AND TRADEMARK OFFICE
CERTIFICATE OF CORRECTION

PATENT NO.    :    5,079,239

DATED         :    January 7, 1992

INVENTOR(S)   :    H. Howard Sun, Sue S. Cross, Frank Koehn, Malika Gunasekera

It is certified that error appears in the above-identified patent and that said Letters Patent is hereby corrected as shown below:

Column 15: line 54:

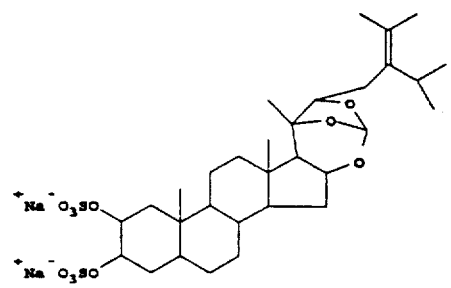 should read 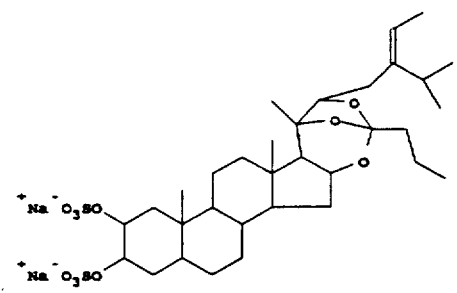

UNITED STATES PATENT AND TRADEMARK OFFICE
CERTIFICATE OF CORRECTION

PATENT NO.    :    5,079,239

DATED         :    January 7, 1992

INVENTOR(S)   :    H. Howard Sun, Sue S. Cross, Frank Koehn, Malika Gunasekera

It is certified that error appears in the above-identified patent and that said Letters Patent is hereby corrected as shown below:

Column 16: line 27:

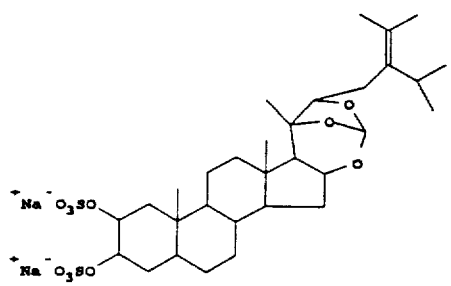 should read 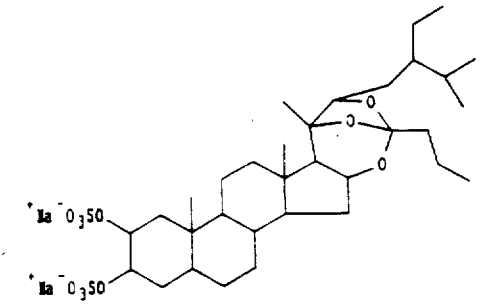

Signed and Sealed this

Sixth Day of July, 1993

Attest:

MICHAEL K. KIRK

Attesting Officer      Acting Commissioner of Patents and Trademarks